US011896228B2

(12) United States Patent
Fleury et al.

(10) Patent No.: US 11,896,228 B2
(45) Date of Patent: Feb. 13, 2024

(54) DEVICES, SYSTEMS, AND METHODS FOR TISSUE RESECTION

(71) Applicant: Boston Scientific Scimed, Inc., Maple Grove, MN (US)

(72) Inventors: Sean P. Fleury, Minneapolis, MN (US); Eric Wespi, Maple Grove, MN (US); Nicholas L Tassoni, Andover, MN (US); Brian J. Hanson, Shoreview, MN (US); Gregory Y. Lee, Eden Prairie, MN (US); Jose A. Meregotte, Blaine, MN (US); Anthony F. Tassoni, Jr., Andover, MN (US); Kevin Windheuser, Hopkinton, MA (US); John A. Hingston, Framingham, MA (US); Nolan Hobart, Milford, MA (US); Michael E. Zupkofska, Rockland, MA (US); Ryan V. Wales, Northborough, MA (US); Scott E. Brechbiel, Acton, MA (US); Rachael Campion, Boston, MA (US); Tara A. Jarobski, North Oxford, MA (US); Danny S. Lee, Cambridge, MA (US); Alexander J. Burnham, Southbury, CT (US); Christopher K. Oto, Boston, MA (US); Nicholas J. Mazzola, Hudson, MA (US); Kevin L Bagley, Dedham, MA (US); Shaun D. Comee, Fiskdale, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1182 days.

(21) Appl. No.: 16/408,906

(22) Filed: May 10, 2019

(65) Prior Publication Data
US 2019/0343528 A1 Nov. 14, 2019

Related U.S. Application Data

(63) Continuation of application No. 62/670,274, filed on May 11, 2018.

(51) Int. Cl.
*A61B 18/00* (2006.01)
*A61B 17/00* (2006.01)
(Continued)

(52) U.S. Cl.
CPC .......... *A61B 17/1114* (2013.01); *A61B 1/018* (2013.01); *A61F 2/04* (2013.01);
(Continued)

(58) Field of Classification Search
CPC .. A61B 2017/00269; A61B 2017/0034; A61B 2017/00592; A61B 2017/00579;
(Continued)

(56) References Cited

U.S. PATENT DOCUMENTS

| 6,613,078 B1 | 9/2003 | Barone |
|---|---|---|
| 7,338,505 B2 | 3/2008 | Belson |

(Continued)

OTHER PUBLICATIONS

Atala, A., Lanza, R., Mikos, A., Nerem, R., eds., "Principles of Regenerative Medicine—Third Edition", (UK—Elsevier Inc.) 1454 pages (2018).
(Continued)

*Primary Examiner* — Joseph A Stoklosa
*Assistant Examiner* — Annie L Shoulders
(74) *Attorney, Agent, or Firm* — Seager, Tufte & Wickhem, LLP

(57) ABSTRACT

Exemplary embodiments of the present disclosure relate to devices, systems, and methods for tissue resection in a body lumen of a patient, and may include an endoscope and a backstop delivery device extendable through the endoscope. The backstop delivery device may deliver a backstop to a
(Continued)

location of selected tissue for resection. A backstop may include a covering being deployable in a patient. The covering may have one or more anchoring mechanisms disposed on an edge of the covering. A tissue resecting device may be extendable through the endoscope for resecting the selected tissue for resection. The covering may be deployable to an outer surface of the body lumen, such that the anchoring mechanism may secure the covering to the outer surface of the body lumen and the covering may expand to cover the selected tissue for resection.

9 Claims, 11 Drawing Sheets

(51) Int. Cl.
*A61F 2/00* (2006.01)
*A61B 17/32* (2006.01)
*A61B 17/11* (2006.01)
*A61B 1/018* (2006.01)
*A61F 2/04* (2013.01)
*A61L 27/36* (2006.01)
*A61B 17/06* (2006.01)
*A61B 17/08* (2006.01)

(52) U.S. Cl.
CPC ..... *A61L 27/3633* (2013.01); *A61B 17/06166* (2013.01); *A61B 17/083* (2013.01); *A61B 2017/0034* (2013.01); *A61B 2017/00269* (2013.01); *A61B 2017/00579* (2013.01); *A61B 2017/00592* (2013.01); *A61B 2017/00623* (2013.01); *A61B 2017/00867* (2013.01); *A61B 2017/00951* (2013.01); *A61B 2017/1132* (2013.01); *A61B 2018/00494* (2013.01); *A61B 2018/00595* (2013.01); *A61F 2002/045* (2013.01)

(58) Field of Classification Search
CPC ........... A61B 2017/00626; A61B 2017/00867; A61B 2018/00494; A61B 2018/00595
See application file for complete search history.

(56) References Cited

U.S. PATENT DOCUMENTS

| | | | |
|---|---|---|---|
| 8,590,764 B2 | 11/2013 | Hartwick et al. | |
| 8,911,458 B2 | 12/2014 | Bassan et al. | |
| 9,155,539 B2 | 10/2015 | Gronberg et al. | |
| 9,295,470 B2 | 3/2016 | Baur et al. | |
| 9,743,931 B2 | 8/2017 | Gronberg | |
| 9,820,746 B2 | 11/2017 | Imran | |
| 10,130,502 B2 | 11/2018 | Chamorro et al. | |
| 10,307,280 B2 | 6/2019 | Zeiner et al. | |
| 10,420,665 B2 | 9/2019 | Sharma et al. | |
| 10,548,753 B2 | 2/2020 | Rousseau | |
| 2010/0106068 A1* | 4/2010 | Karpiel | A61B 17/0057 602/42 |
| 2014/0107709 A1 | 4/2014 | Schmitz et al. | |
| 2014/0180436 A1* | 6/2014 | Keane | A61B 17/0057 623/23.72 |
| 2015/0005394 A1* | 1/2015 | Scopton | A61B 17/3478 514/772.1 |
| 2015/0080945 A1 | 3/2015 | Michalak | |
| 2016/0000550 A1 | 1/2016 | Nagle | |
| 2016/0045552 A1 | 2/2016 | Ramer et al. | |
| 2017/0281181 A1 | 10/2017 | Matonick et al. | |
| 2018/0296220 A1* | 10/2018 | Zein | A61B 17/0467 |

OTHER PUBLICATIONS

McAteer H., et al, "Cost-effectiveness analysis at the development phase of a potential ealth technology: examples based on tissue engineering of bladder and urethra", J. Tissue Eng. Regen.Med. 1(5):343-349 (2007).
Atala, A., et al., "Tissue-engineered autologous bladders for patients needing cystoplasty", Lancet 367:1241-1246 (2006).
International Search Report and Written Opinion for International application No. PCT/US2019/031715, dated Aug. 5, 2019, 12 pages.
Author unknown, "Laboratory-grown urethras implanted in patients, scientists report", ScienceDaily [online], Mar. 2011 [retrieved on Oct. 29, 2019]. Retrieved from Internet URL: https://www.sciencedaily.com/releases/2011/03/110307184632.htm, 4 pages.

* cited by examiner

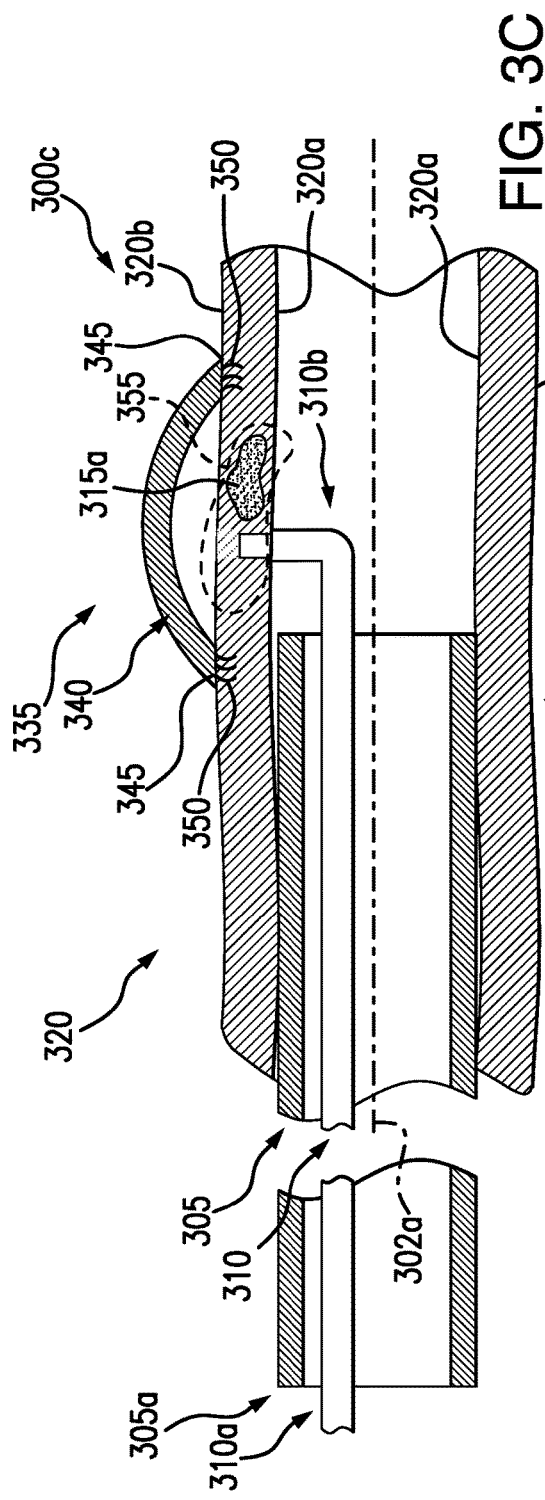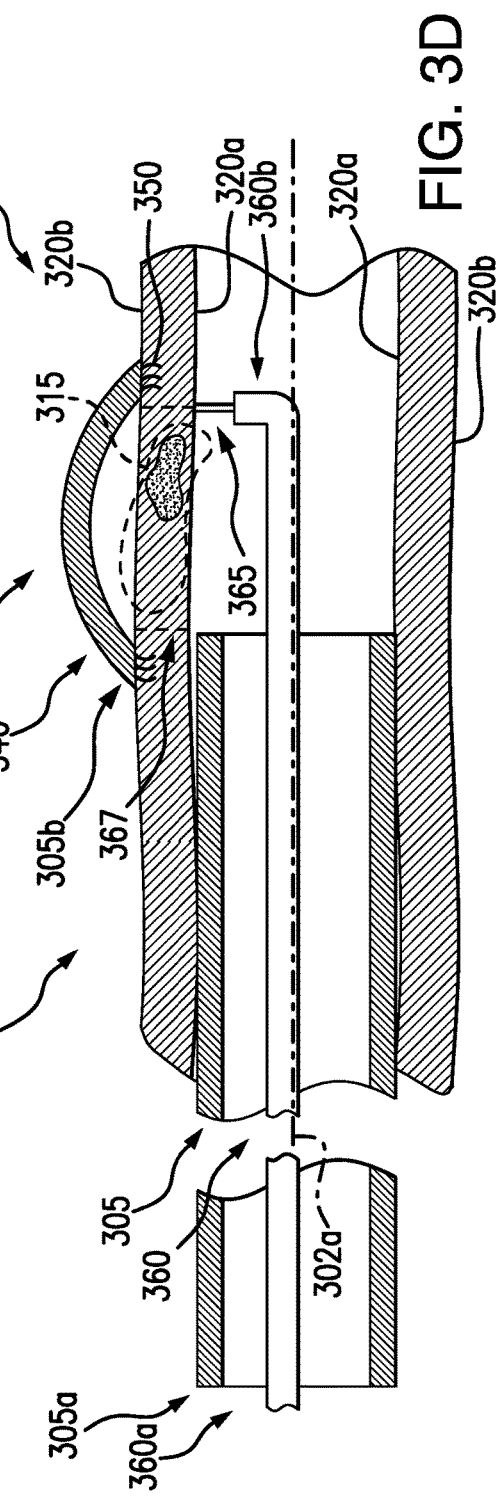

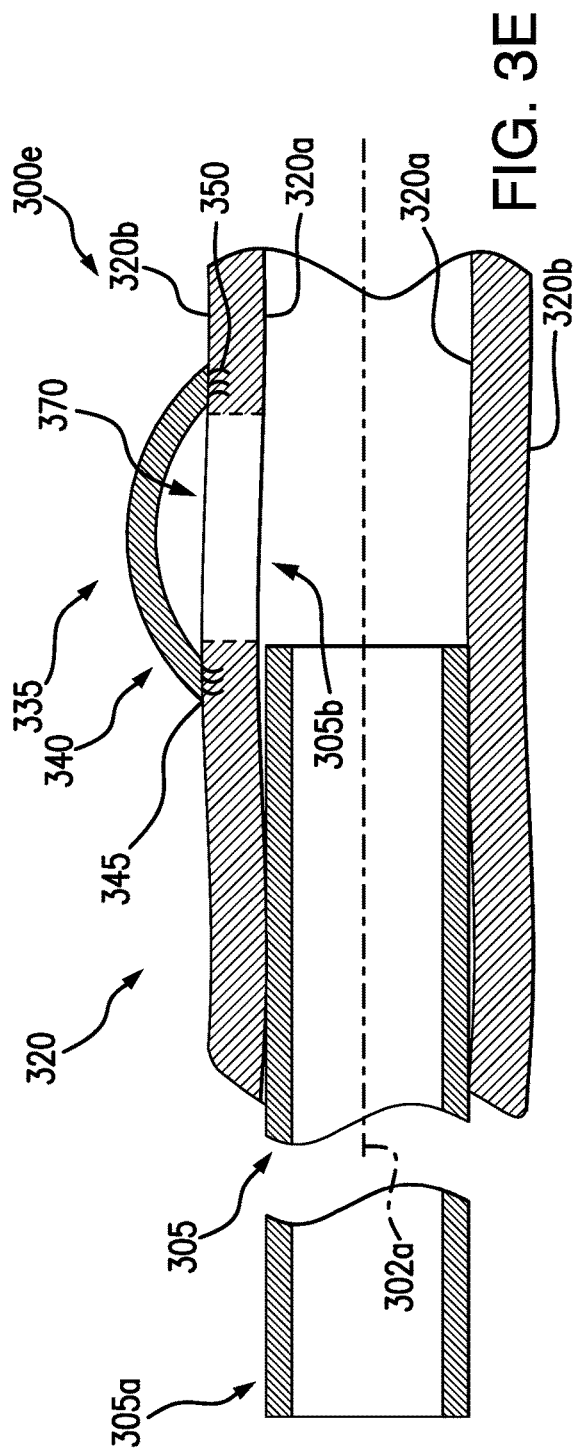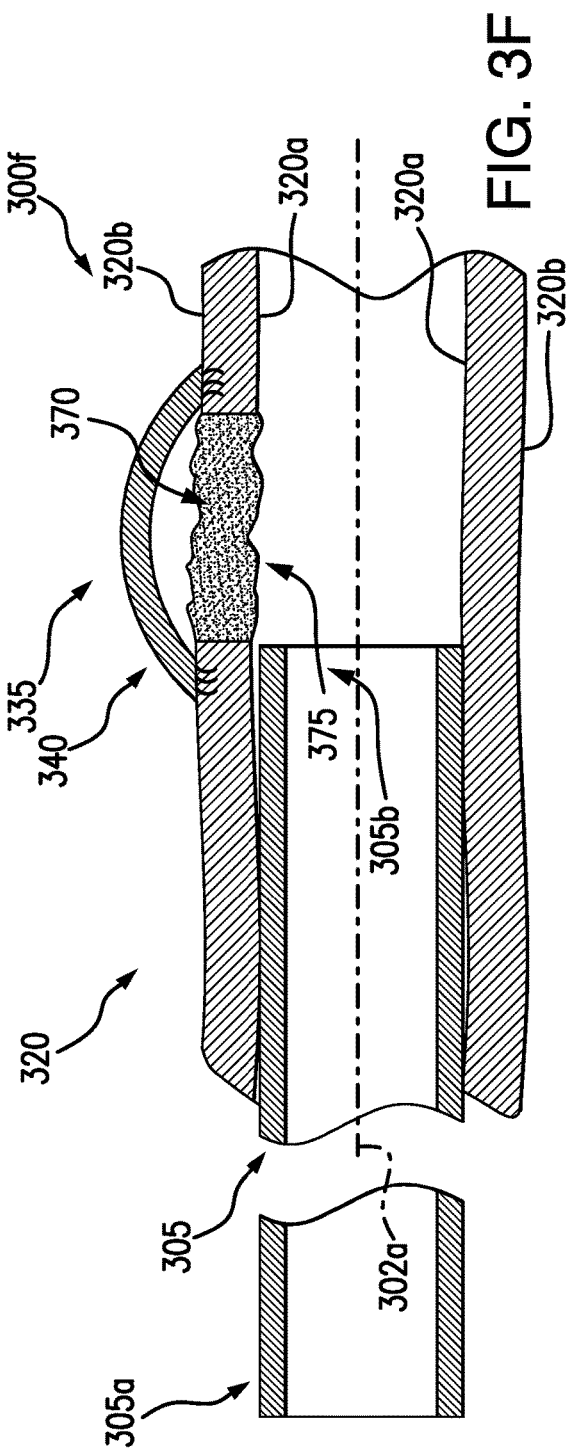

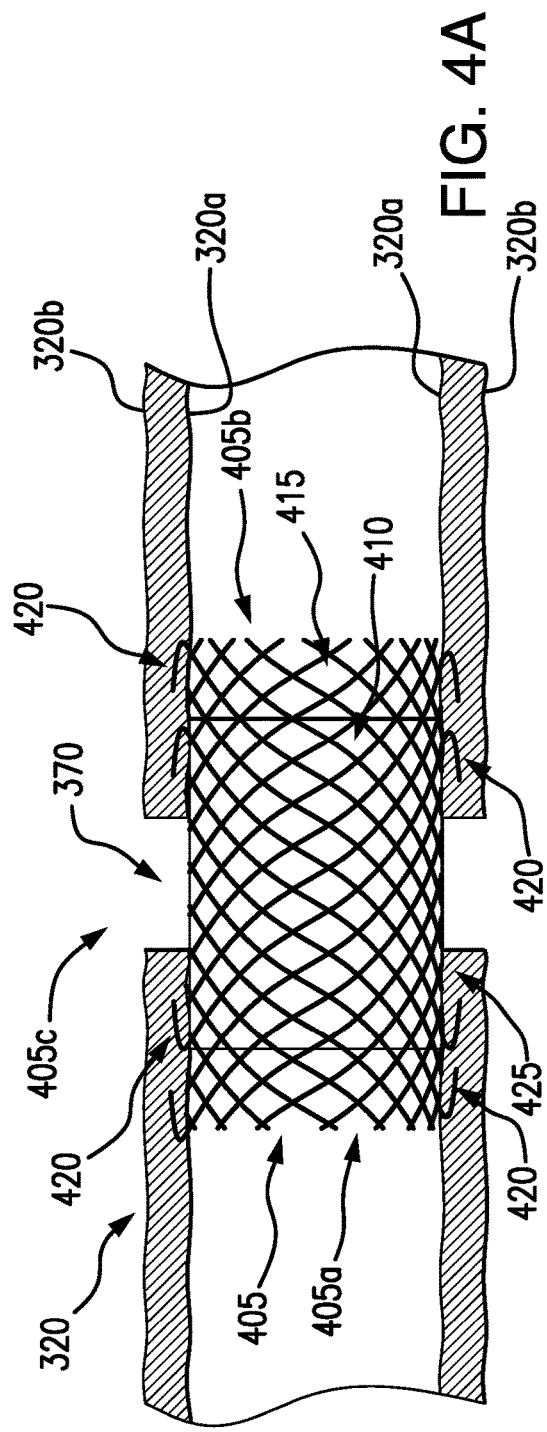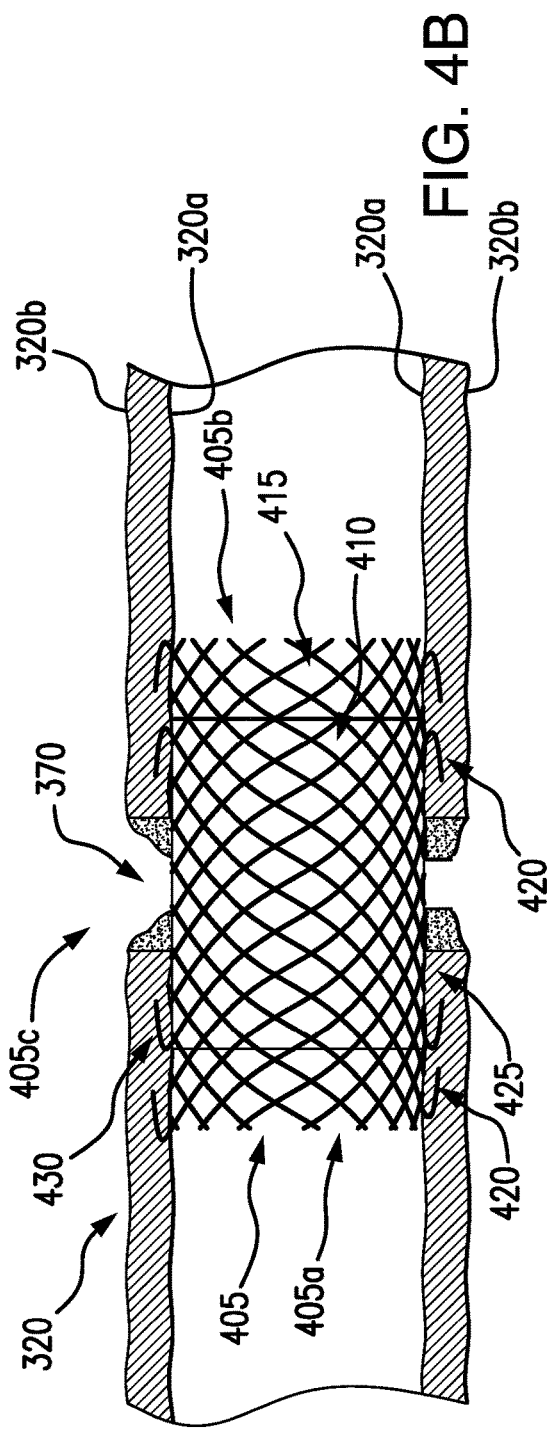

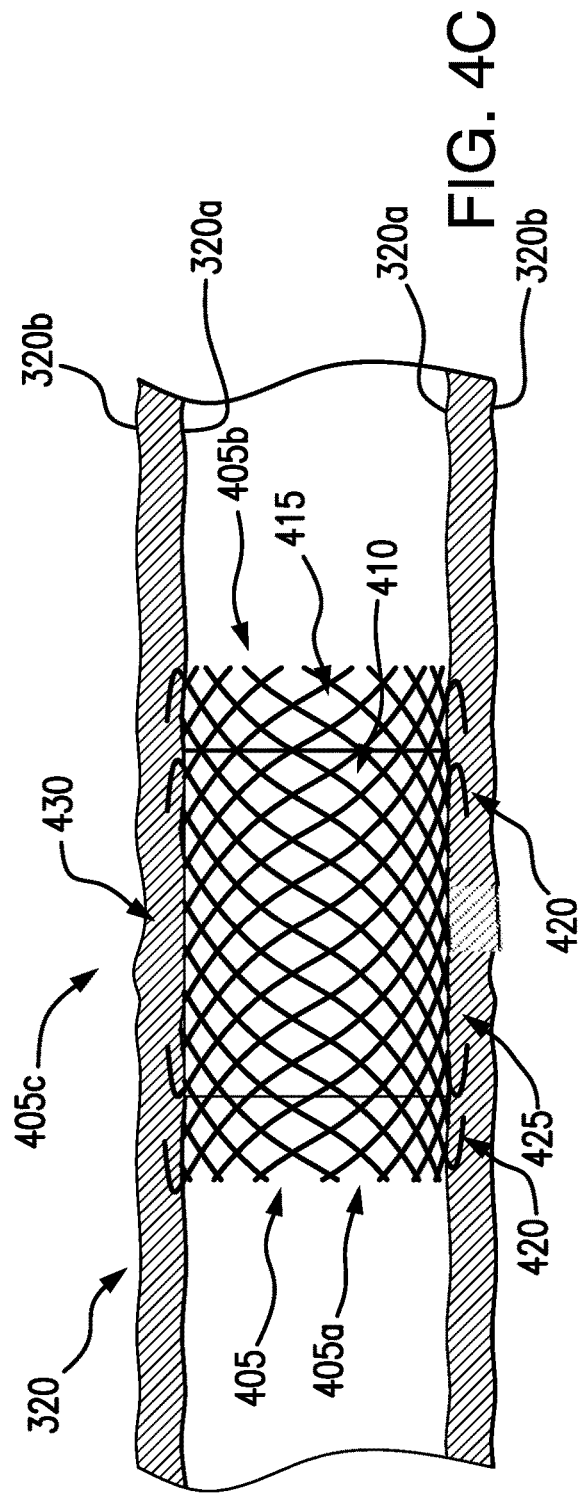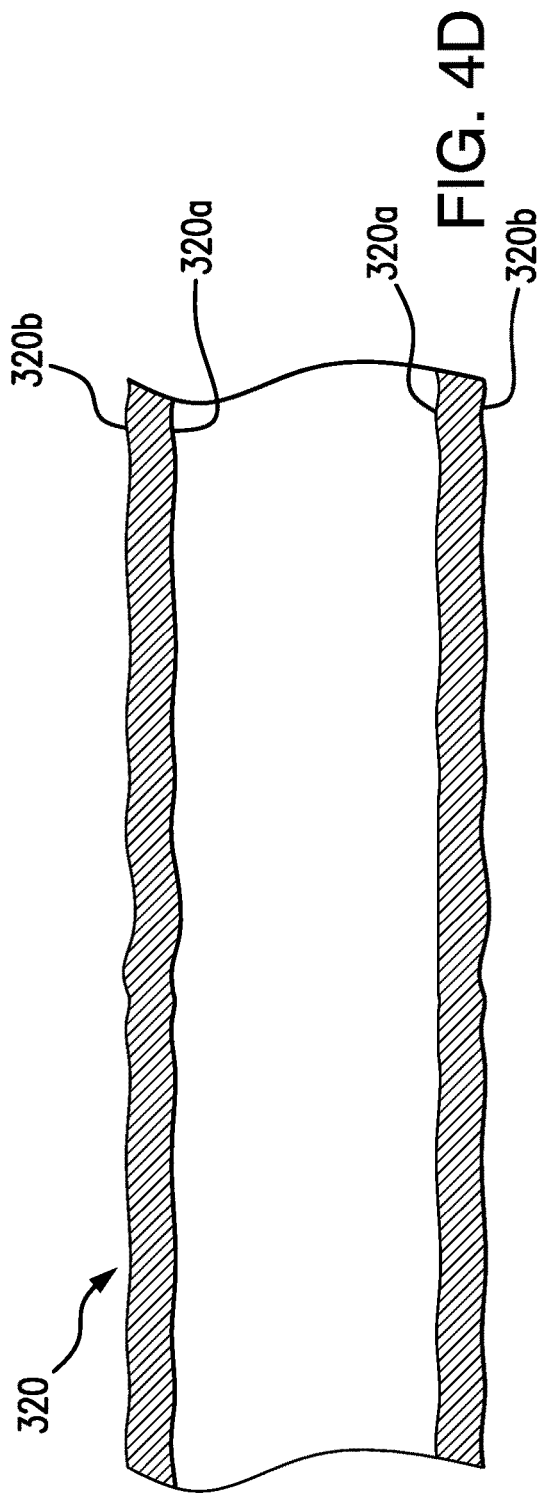

Table 1

| Product | Company | Material | Processing | Form |
|---|---|---|---|---|
| AlloDerm® | LifeCell | Human skin | Natural | Dry sheet |
| AlloPatch® | Musculoskeletal Transplant Foundation | Human fascia lata | Natural | Dry sheet |
| Axis™ dermis | Mentor | Human dermis | Natural | Dry sheet |
| Bard® Dermal Allograft | Bard | Cadaveric human dermis | Natural | Dry sheet |
| CollaMend™ | Arthrotek | Porcine small intestinal submucosa (SIS) | Cross-linked | Hydrated sheet |
| DurADAPT™ | Pegasus Biologicals | Horse pericardium | Cross-linked | Dry sheet |
| Dura-Guard® | Synovis Surgical | Bovine pericardium | Cross-linked | Hydrated sheet |
| Durasis® | Cook SIS | Porcine small intestinal submucosa (SIS) | Natural | Dry sheet |
| Durepair® | TEI Biosciences | Fetal bovine skin | Natural | Dry sheet |
| FasLata® | Bard | Cadaveric fascia lata | Natural | Dry sheet |
| Graft Jacket® | Wright Medical Tech | Human skin | Natural | Dry sheet |
| Oasis | Healthpoint | Porcine small intestinal submucosa (SIS) | Natural | Dry sheet |
| OrthADAPT™ | Pegasus Biologicals | Horse pericardium | Cross-linked | Dry sheet |
| Pelvicol® | Bard | Porcine dermis | Cross-linked | Hydrated sheet |
| Peri-Guard® | Synovis Surgical | Bovine pericardium | Cross-linked | Dry sheet |
| Permacol™ | Tissue Science Laboratories | Porcine skin | Cross-linked | Hydrated sheet |
| PriMatrix™ | TEI Biosciences | Fetal bovine skin | Natural | Dry sheet |
| Restore™ | DePuy | Porcine small intestinal submucosa (SIS) | Natural | Dry sheet |
| Stratasis® | Cook SIS | Porcine small intestinal submucosa (SIS) | Natural | Dry sheet |
| SurgiMend™ | TEI Biosciences | Fetal bovine skin | Natural | Dry sheet |
| Suspend® | Mentor | Human fascia lata | Natural | Dry sheet |
| TissueMend® | TEI Biosciences | Fetal bovine skin | Natural | Dry sheet |
| Vascu-Guard® | Synovis Surgical | Bovine pericardium | Cross-linked | Dry sheet |
| Veritas® | Synovis Surgical | Bovine pericardium | Cross-linked | Dry sheet |
| Kelsus™ | Medcycle | ECM protein, PGA, water | | Gel |
| Xenform™ | TEI Biosciences | Fetal bovine skin | Natural | Dry sheet |
| Zimmer Collagen Patch® | Tissue Science Laboratories | Porcine dermis | Cross-linked | Hydrated sheet |

FIG. 5

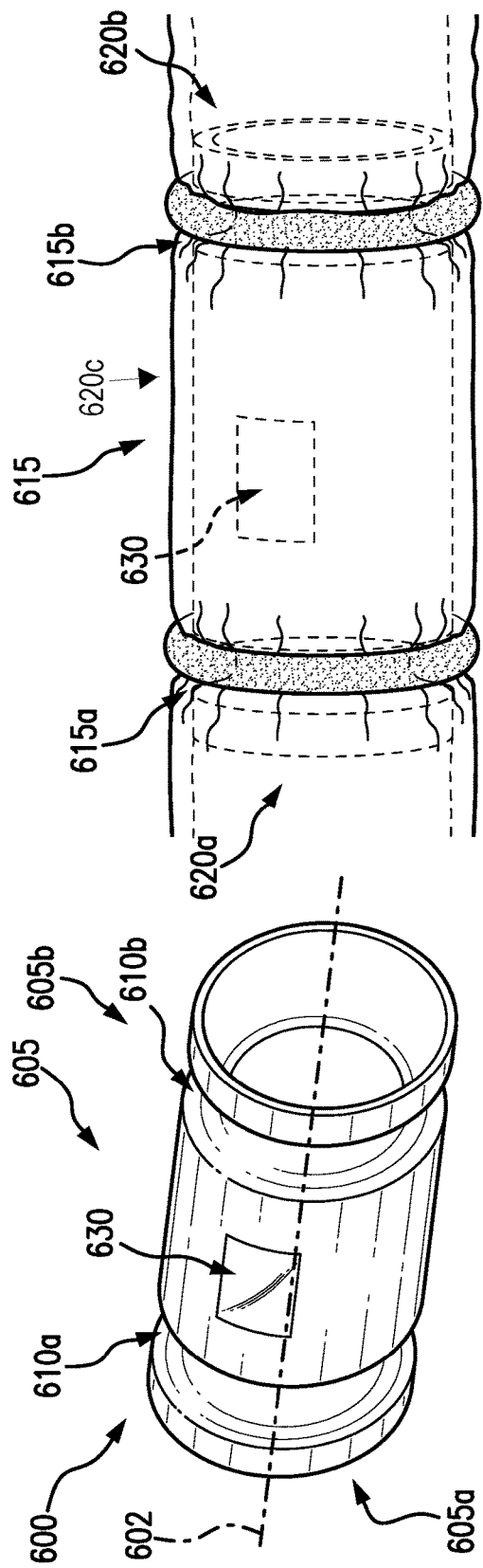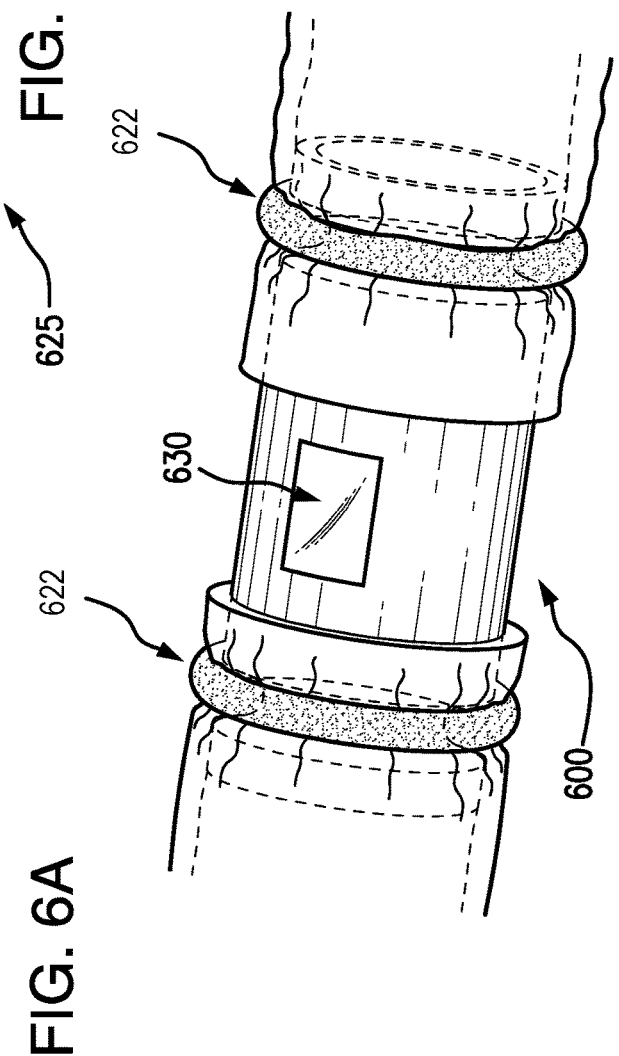

DEVICES, SYSTEMS, AND METHODS FOR TISSUE RESECTION

CROSS REFERENCE TO RELATED APPLICATIONS

This application claims the benefit of priority under 35 U.S.C. § 119 to U.S. Provisional Patent Application Ser. No. 62/670,274, filed on May 11, 2018, which is incorporated by reference in its entirety for all purposes.

FIELD

The present disclosure relates generally to devices, systems, and methods for performing endoscopic procedures, and, more particularly, tissue resection devices for endoscopic mucosal resection (EMR) and/or endoscopic submucosal dissection (ESD) procedures, including such devices, system and methods to achieve partially or fully circumferential endoscopic full thickness resection (eFTR), tissue closure and/or tissue apposition.

BACKGROUND

Endoscopic mucosal resection (EMR) and/or endoscopic submucosal dissection (ESD) procedures may be used to remove benign or diseased tissue, e.g., lesions, cancerous tumors, and/or other anomalies, from a patient's gastrointestinal system. In some patients, full thickness resection (FTR), which may be partially or fully circumferential in a body lumen, may be necessary to ensure complete removal of the diseased tissue, as opposed to removal, e.g., only the of mucosal layers of the gastrointestinal system.

However, FTR procedures may pose additional challenges such as anatomical difficulties of removing tissue adjacent critical internal organs and other sensitive structures, as well as risk of post-operative leakage, potentially increasing a patient's health risk in undergoing an FTR procedure.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

According to an exemplary embodiment of the present disclosure, a system for tissue resection in a body lumen of a patient may include an endoscope and a backstop delivery device. The backstop delivery device may be extendable through the endoscope and positionable in the body lumen at a location of selected tissue for resection. The system may further include a backstop, which may have a covering that is deployable by the backstop delivery device, and a tissue resecting device, which may be extendable through the endoscope for resecting the selected tissue for resection. The covering may be deployable to an outer surface of the body lumen, such that one or more anchoring mechanisms disposed on an edge of the covering may be securable to the outer surface of the body lumen and the covering may be expandable to cover the selected tissue for resection.

In various of the foregoing and other embodiments of the present disclosure, the backstop delivery device may include a tissue penetrating device for insertion into the selected tissue for resection. The tissue penetrating device may be extendable partially in the selected tissue for resection so as to stabilize the backstop delivery device. The covering may be formed of a self-expanding material. The covering may have a relaxed shape memory curvature comprising an arc shape. The arc shape of the curvature and the edge of the covering may be conformable to a curvature of the outer surface of the body lumen. The one or more anchoring mechanisms may be a mechanical fastener, a suture, or an adhesive, or combinations thereof. The mechanical fasteners may be hooks, barbs, clips, or clamps, or combinations thereof. The tissue resecting device may be a cautery tool including a distal tip for cauterizing tissue around a perimeter of the selected tissue for resection. The edge of the covering of the backstop may be configured to extend beyond the perimeter of the selected tissue for resection such that the one or more anchoring mechanisms may remain securable to the outer surface of the body lumen after resection of the selected tissue.

According to an exemplary embodiment of the present disclosure, a tissue resection device may include a backstop, which may have a covering deployable in a patient. The covering may have one or more anchoring mechanisms disposed on an edge of the covering. The covering may be deployable to an outer surface of a body lumen of a patient at a location of selected tissue for resection, such that the one or more anchoring mechanisms may be configured to secure the covering to the outer surface of the body lumen. The covering may be self-expandable to cover the selected tissue for resection.

In various of the foregoing and other embodiments of the present disclosure, the covering may be formed of a self-expanding material. The covering may have a relaxed shape memory curvature comprising an arc shape. The arc shape of the curvature and the edge of the covering may be conformable to a curvature of the outer surface of the body lumen. The one or more anchoring mechanisms may be a mechanical fastener, a suture, or an adhesive, or combinations thereof. The mechanical fasteners may be hooks, barbs, clips, or clamps, or combinations thereof. The edge of the covering of the backstop may be configured to extend beyond a perimeter of the selected tissue for resection such that the one or more anchoring mechanisms may remain securable to the outer surface of the body lumen after resection of the selected tissue.

According to an exemplary embodiment of the present disclosure, a method for resection of selected tissue in a body lumen of a patient may include inserting an endoscope in the body lumen of the patient to a location of the selected tissue, and inserting a backstop delivery device through the endoscope to the selected tissue. The method may further include deploying a backstop, which may include a covering to an outer surface of the body lumen at the location of the selected tissue with the backstop delivery device. The covering may have one or more anchoring mechanisms disposed on the covering. The method may further include securing the one or more anchoring mechanisms of the covering to the outer surface of the body lumen and expanding the covering to cover the selected tissue for resection, and resecting the selected tissue by a tissue resecting device.

In various of the foregoing and other embodiments of the present disclosure, the method may further include inserting a tissue penetrating device of the backstop delivery device into the selected tissue for resection. The covering may be formed of a self-expanding material. The covering may have a relaxed shape curvature comprising an arc shape. The tissue resecting device may be a cautery tool including a distal tip for cauterizing tissue around a perimeter of the selected tissue for resection. An edge of the covering may be extendable beyond the selected tissue for resection such that the one or more anchoring mechanisms may be secure to the outer surface of the body lumen after resection of the selected tissue.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 3A-3G illustrate exemplary embodiments of a tissue resection system and method for tissue resection in accordance with the present disclosure;

FIGS. 4A-4D illustrate an exemplary embodiment of a tissue closure device and method for tissue closure in accordance with the present disclosure;

FIG. 5 illustrates a chart of exemplary embodiments of an extracellular matrix (ECM) material for tissue closure in accordance with the present disclosure; and FIGS. 6A-6C illustrate an exemplary embodiment of a tissue resection device in accordance with the present disclosure.

DETAILED DESCRIPTION

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

It may be understood that references to "proximal" may be defined as an end of the systems and devices closest to the entry point of the patient and "distal" may be defined as an end of the systems and devices closest to the desired location of the system and devices in the patient (e.g., a patient's gastrointestinal system).

Figure 1:
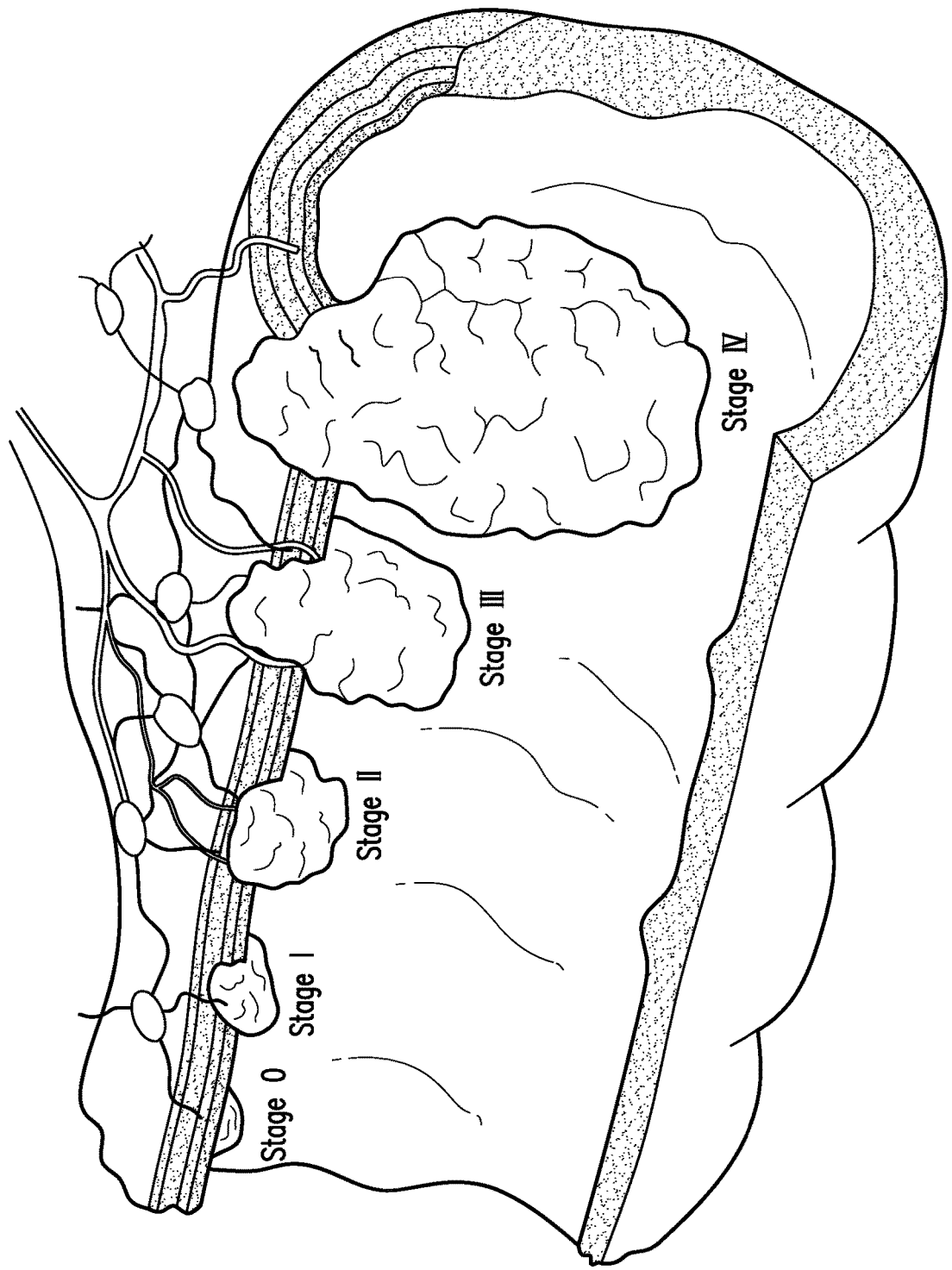
FIG. 1 illustrates a body lumen of a patient.

As described above, patients with diseased or other tissue in the gastrointestinal system may require resection. Referring to FIG. 1, various sized lesions are illustrated in a body lumen (e.g., gastrointestinal system) of a patient. As shown, earlier stages of diseased tissue may not extend through all the layers of the body lumen, which may allow for resection of only the affected tissue layers. However, as diseased tissue advances to later stages, resection of the entire tissue portion (e.g., full thickness resection) may be needed to fully excise the diseased tissue from the patient. Exemplary embodiments of devices, systems, and methods for partial or full thickness tissue resection in accordance with the present disclosure may allow for a selected tissue section containing diseased tissue to be contained and resected from surrounding tissue, the surrounding tissue then being joined together to close a gap formed by the resection of the selected tissue. In some embodiments, the tissue resection may be fully circumferential, e.g., extending 360° around a body lumen. In other embodiments, the tissue resection may be partially circumferential, e.g., extending less than 360° around a body lumen. Although "resection" is used throughout the disclosure, exemplary embodiments of the present disclosure may encompass resecting, dissecting, removing, ablating, cutting vaporizing, freezing, etc., and may be full thickness, partial thickness, and in instances of a procedure occurring in a body lumen, may be partial and/or fully circumferential.

According to exemplary embodiments of the present disclosure, an intermediary device may be utilized to secure a body lumen tissue prior to a resection procedure. In some embodiments, a backstop may be used to cover a portion of a body lumen, e.g., a selected area of tissue for resection. It is understood that the backstop may be utilized in partial and/or full circumferential full thickness resection procedures. In some embodiments, a stent may be used to extend between a selected area of tissue for resection. For example, the backstop and/or stent may be configured to attach to an outer or inner surface of the body lumen, and fully encompass the selected area of tissue for resection. When the tissue is resected, the backstop and/or stent may hold the remaining lumen tissue together, and in some embodiments may aid in closing the resected area. In embodiments, the backstop and/or stent may also minimize and/or prevent contamination of other body fluids into the body lumen. Although the body lumen is described with respect to the gastrointestinal system, including but not limited to an intestine, colon, and/or duodenum, it is understood that exemplary embodiments of devices, systems, and methods of the present disclosure may apply to any body lumen in a patient.

Figure 2:
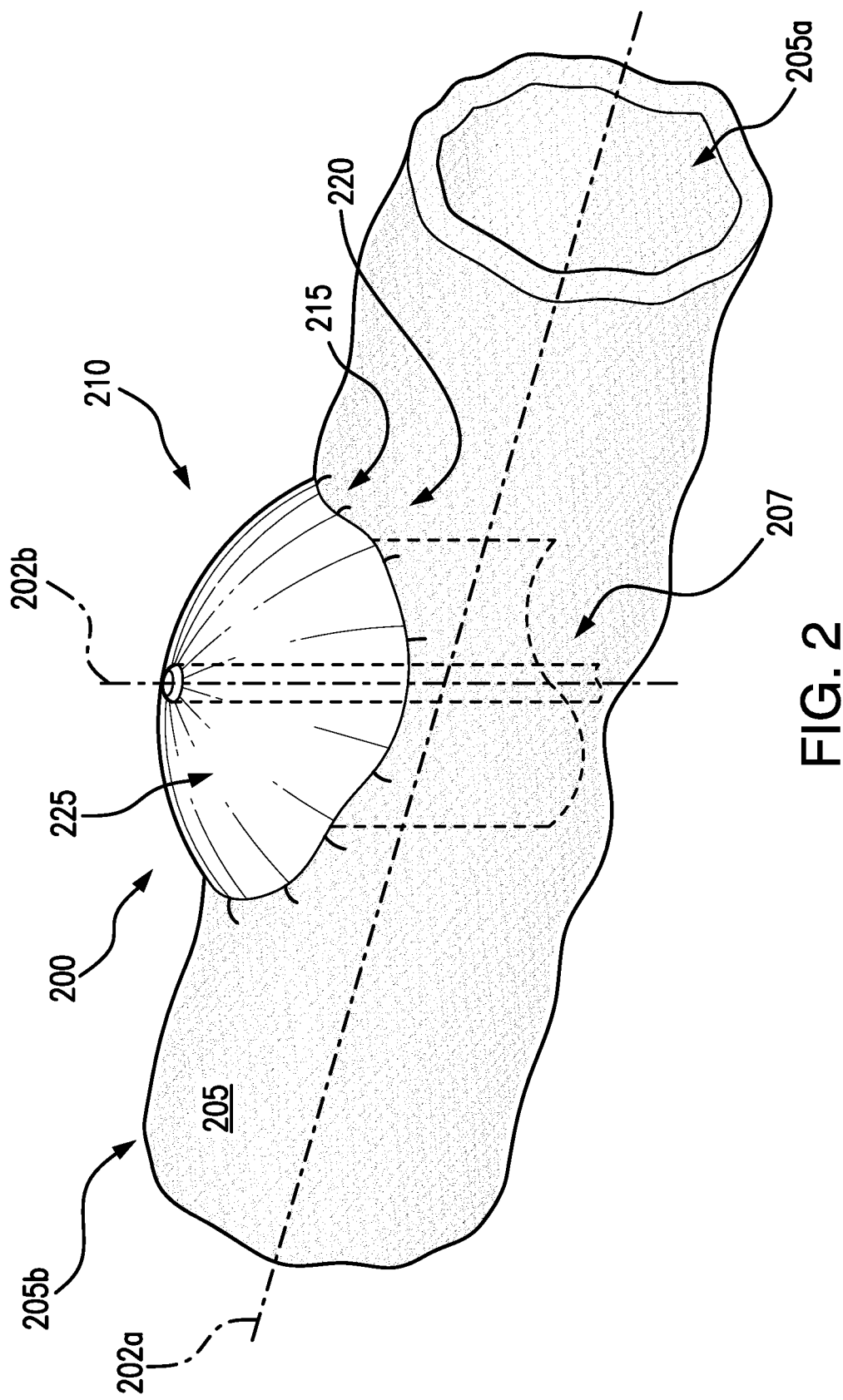
FIG. 2 illustrates an exemplary embodiment of a backstop in accordance with the present disclosure.

Referring now to FIG. 2, an exemplary embodiment of an intermediary device, e.g., a backstop device 200, for a tissue resection system in accordance with the present disclosure is shown. A backstop 200 may be deployable to cover a selected area of tissue for resection, and may be deployable by a delivery device described in FIGS. 3A-3G. In embodiments, the backstop 200 may be deliverable to a location selected tissue for resection in a patient by an endoscope, gastroscope, colonoscope, duodenoscope, or other known delivery system. An endoscope may be positioned to a desired body lumen tissue, e.g., a gastrointestinal lumen of a patient, in a direction along axis 202*a* (see FIG. 3A). The backstop 200 may be deployable in a direction along axis 202*b*, which may be substantially perpendicular to the axis 202*a*. For example, the backstop 200 may be deployable in a direction transverse to a body lumen. In some embodiments, the backstop 200 may be deployable in a transverse direction by a delivery device (see FIGS. 3A-3G).

The backstop 200 may include a covering 210. The covering 210 may be formed of a self-expanding material, such as a shape memory material (e.g., nitinol). In some embodiments, the covering 210 may be a mesh or braided wire. In other embodiments, the covering 210 may be a film or other type of matrix having cells between a braid or weave of shape memory material. The backstop 200 may be held in the delivery device so that the covering is in a constrained configuration. When the backstop 200 is delivered to the selected area of tissue for resection, e.g., an outer surface 205*b* of tissue 205 (e.g., a body lumen tissue), the covering 210 may expand to a pre-set shape to an expanded configuration. In embodiments, the backstop 200 may be deliverable from a body lumen, e.g., by extending through tissue 205 from an inner surface 205*a* to an outer surface 205*b*. In some embodiments, the backstop 200 may be delivered directly to an outer surface 205*b* of the tissue 205, e.g., laparoscopically. A stem, or inner sheath 207, may be deployable from the endoscope, for delivery of the covering 210 to the desired position in the patient tissue. The inner sheath 207 may be separatable from the covering 210 once the covering is in position, e.g., by fasteners or other known joining mechanisms.

An edge 215 of the covering 210 may include one or more anchoring mechanisms 220 for attaching the covering 210 to the outer surface 205*b* of the tissue 205. For example, the edge 215 may extend around a perimeter of the covering 210 and may be any shape configured to cover an area of the selected tissue for resection in the body lumen. In some embodiments the covering 210 may be in any shape including but not limited to circular, elliptical, square, polygonal, and the like. In embodiments, the anchoring mechanism 220 may be any type of mechanical fasteners such as hooks, barbs, clips, and/or clamps. In some embodiments, the anchoring mechanism 220 may be a suture, and/or adhesive. Different combinations of the anchoring mechanisms 220 may be utilized. The anchoring mechanism 220 may be configured to embed or otherwise attach to the outer surface 205*b* of the tissue 205 to secure the backstop 200 in a desired position.

The covering 210 may be heat-set to a pre-set shape, and may be formed having a curvature, or arc shape, e.g., substantially spherical or semi-spherical shape. In embodiments, the covering 210 may be self-expandable to an umbrella shape, so that the anchoring mechanism 220 secures the backstop 200 to the tissue 205, and expands in a direction away from the outer surface 205*b* of the tissue 205. In embodiments, the pre-set arc shape of the covering 210 may cause the edge 215 of the covering 210 to conform to a curvature of the outer surface 205*b* of the body lumen tissue 205 (e.g., intestine). The arc shape may also allow the covering to embed the anchoring mechanism 220 within the tissue 205 by a force of the shape memory material expanding to the arc shape. A space 225 may be created between the covering 210 and the outer surface 205*b* of the tissue 205, which may provide a clearance during tissue resection, e.g., cutting, to remove the selected tissue. By forming the covering 210 to have an arc shape, the space 225 may minimize a risk of a tissue resecting device inadvertently damaging the covering 210.

Figure 3A:
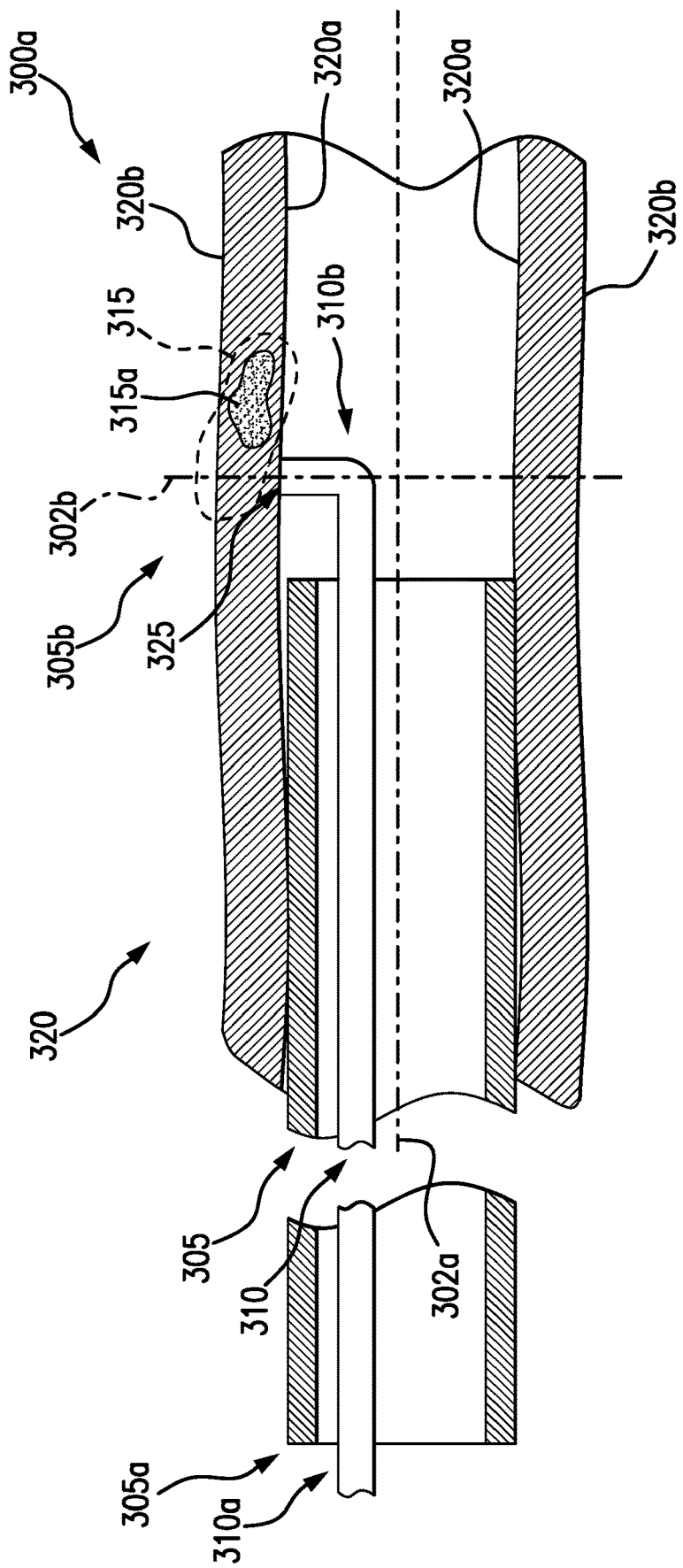

Referring now to FIGS. 3A-3G, exemplary embodiments of tissue resection delivery systems and methods for tissue resection in accordance with the present disclosure are shown. In embodiments, and as shown in FIG. 3A at step 300*a*, an endoscope 305, or gastroscope, colonoscope, duodenoscope, or the like, may be inserted into a body lumen 320 of a patient in a direction along axis 302*a* and may be positioned at a location of selected tissue for resection indicated by reference numeral 315. It is understood that selected tissue for resection 315 may be an area of diseased tissue, e.g., including tumors, cysts, and/or lesions 315*a*, as well as a portion of healthy tissue immediately adjacent the diseased tissue 315. A portion of healthy tissue may be resected to minimize a risk of not fully capturing the diseased tissue and/or dislodging diseased tissue cells to potentially contaminate another tissue region. In some embodiments, the selected tissue for resection may include a benign cyst or lesion.

The endoscope 305 may be positionable in direction along axis 302*a* in a body lumen in a patient's gastrointestinal system so that a distal end 305*b* of the endoscope 305 may be positionable for accessing the tissue selected for resection. It is understood that a proximal end 305*a* of an endoscope 305 may be positioned external to a patient. A medical professional may determine a position of the endoscope 305 relative to the tissue selected for resection 315 by known visualization techniques such as direct visualization, ultrasonic imaging, and/or fluoroscopy and/or radiopaque markers. For example, the tissue selected for resection 315 may be marked at the boundaries, e.g., distal and proximal of the diseased tissue 315*a*. The endoscope 305 may also include an imaging device such as a camera, so that the medical professional may visualize the tissue selected for resection 315 for positioning. The distal end 305*b* of the endoscope 305 may be positionable by the medical professional by actuating the proximal end 305*a* of the endoscope 305, e.g., by a handle.

A backstop delivery device 310 may be deliverable to a distal end 305*b* of the endoscope 305, e.g., by a working channel. In some embodiments, the endoscope 305 may not be deliverable to the tissue selected for resection, e.g., the endoscope may have a diameter larger than a diameter of the body lumen including the tissue selected for resection 315. The backstop delivery device 310 may be configured to extend a distance distal to the endoscope 305 to the tissue selected for resection 315. The backstop delivery device 310 may be a lumen, e.g., a hollow tube, extending in a direction along axis 302*a*. In embodiments, a distal tip 325 may be configured to contact an inner surface 320*a* of the body lumen 320. As shown in FIG. 3A, the distal tip 325 may be configured to extend in a direction along axis 302*b*, which may be substantially transverse to axis 302*a*.

In some embodiments, a delivery device may be steerable, in order to fit through a working channel of the endoscope. For example, the delivery device may have one or more (e.g., four) steering wires. The steering wires may extend from the distal end of the delivery device, e.g., in a patient's tissue at a desired location, to the proximal end at a handle, e.g., outside of a patient. The steering wires may be actuable at the handle to cause a tip of the delivery device to bend. The tip of the delivery device may be bendable, for example, up to 90°, relative to the endoscope, or perpendicular to the axis 302*a*. The tip of the delivery device may be bendable in any radial direction for accessing the target tissue. In some embodiments, the tip of the delivery device may be bendable beyond 90°. In some embodiments, the endoscope may be steerable, so that steering wires may not be included in the delivery device. For example, an actuation mechanism disposed at a proximal end of the endoscope (e.g., outside of the patient) may allow the distal end of the endoscope to angle the delivery device to the target tissue.

The backstop delivery device 310 may be extendable distal of the distal end 305*b* of the endoscope 305 to position a distal end 310*b* of the backstop delivery device 310 at the location of the selected tissue for resection. In embodiments, the distal end 310*b* of the delivery device may be positionable proximal to a diseased tissue 315*a*, in an area of tissue selected for resection 315 for deployment of a backstop. In other embodiments, the distal end 310*b* of the delivery device may be positionable distal to a diseased tissue 315a in an area of tissue selected for resection 315 for deployment of the backstop. It is understood that the delivery device may avoid deploying a backstop through a diseased tissue 315a, to minimize a risk of dislodging diseased tissue cells into a patient. A proximal end 310a of a backstop delivery device 310 may be positioned external to a patient. The distal end 310b of the backstop delivery device 310 may be positionable by a medical professional actuating the proximal end 310a of the delivery device 310 external to the patient.

Figure 3B:
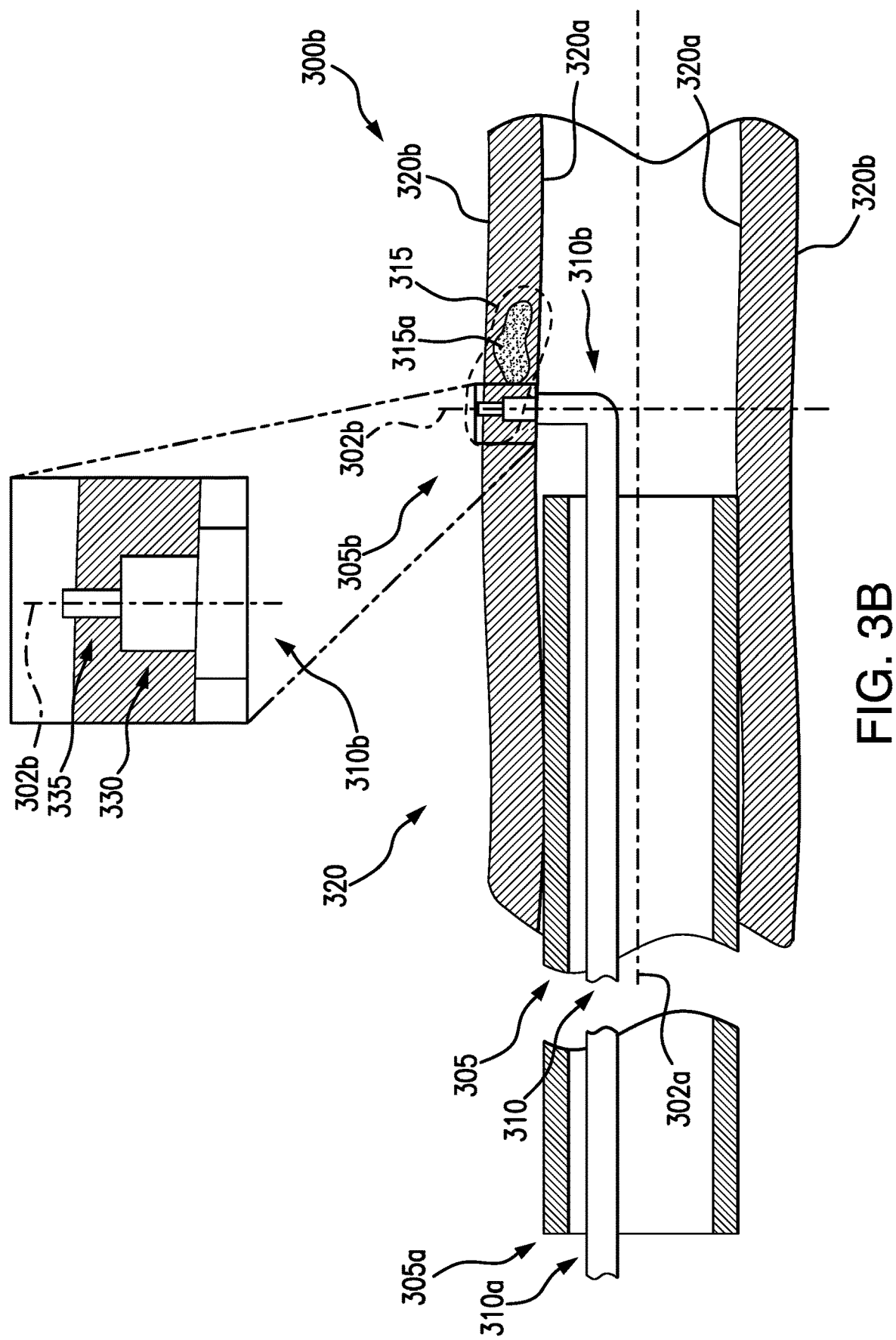

Referring now to FIG. 3B, at step 300b, when the backstop delivery device 310 is positioned as desired for tissue resection, a tissue penetrating device 330 may extend out of the distal end 310b of the backstop delivery device 310, into the inner surface 320a of the body lumen 320. The tissue penetrating device 330 may be any cutting knife, a needle, or other sharp-edged instrument, mechanical or electrical tool, hot or cold, laser, ultrasonic, and/or pneumatic tool, etc., or combination thereof, configured for penetrating the tissue. In embodiments, at least a portion of the tissue penetrating device 330 may be extendable in a direction along the axis 302b, e.g., substantially transverse to axis 302a. In some embodiments, a tip of the tissue penetrating device 330 may be actuatable by a handle at the proximal end. For example, the tip of the tissue penetrating device 330 may be bendable up to approximately 90° in any radial direction. In some embodiments, the tip of the tissue penetrating device 330 may be bendable in an arc-like curve, which may be advantageous for allowing for lower actuation forces and lower tissue penetration forces as compared to a sharp 90° bend.

The tissue penetrating device 330 may extend partially through the body lumen 320, for example, inserting the tissue penetrating device 330 in the inner surface 320a but not extending through the outer surface 320b of the body lumen 320. Inserting the tissue penetrating device 330 partially in body lumen tissue may anchor the backstop delivery device 310 to stabilize for delivering a backstop 335. In some embodiments, the tissue penetrating device 330 may include a hollow tube so that the backstop 335 may be deliverable from the tissue penetrating device.

A backstop 335 may be deployable from the backstop delivery device 310, in a direction along the axis 302b, through body lumen 320, e.g., to extend through the outer surface 320b of the body lumen 320. The backstop 335 may have a sharp distal edge to extend through the remaining tissue of the body lumen, e.g., from the stabilizing tissue penetrating device 330. In some embodiments, the backstop 335 may be deployable by an inner sheath and/or guidewire, actuatable by the medical professional at a proximal end 305a of the endoscope 305. The backstop 335 may be partially deployable for position verification by the medical professional, e.g., so that a placement of the backstop 335 on the outer surface 320b of the of the body lumen 320 may be fine-tuned to the desired position before full deployment. In some embodiments, the backstop 335 may be visible to a medical professional under fluoroscopy and/or other imaging techniques for visualization and positioning.

As the backstop 335 extends beyond the outer surface 320b of the body lumen 320, a cover of the backstop 335 (see FIG. 2) may expand to surround the tissue selected for resection 315. As shown in FIG. 3C, at step 300c, a covering 340 of the backstop 335 may be fully deployed on the outer surface 320b of the body lumen 320. For example, an inner sheath (see FIG. 2) may be deployed from the delivery device through the tissue. The covering 340 may be deployable from the inner sheath, e.g., a self-expanding covering 340 may allow the covering 340 to expand to the desired shape over the desired tissue as it exits the inner sheath. In some embodiments, a dual-channel endoscope may be used, so that the backstop 335 may be deliverable and held in position via a first channel and another tool (e.g., a tissue resecting device) may be deliverable via a second channel. A dual-channel endoscope may be advantageous so that by having the ability to deliver tools via separate channels, the backstop 335 may be utilized without the anchors securing the backstop to the outside of the lumen.

As described above, an edge 345 of the covering 340 may be secured to the outer surface 320b of the body lumen 320 by an anchoring mechanism 350 (e.g., a plurality of mechanical fasteners to embed in the body lumen). The edge 345 may define the boundary of the tissue to be resected 315. For example, the tissue to be resected 315 may include a portion of diseased tissue 315a, as well as the surrounding healthy tissue, in a partially circumferential portion of the body lumen 320. The covering 340 may self-expand in an arc-shape by virtue of being formed of a shape memory material and being pre-set to a curved configuration, so a space 355 may separate the arc-shape of the covering 340 and the outer surface 320b of the body lumen 320. It is understood that the edge 345 maintains contact with the outer surface 320b of the body lumen 320 to ensure a sterile barrier. When the backstop 335 is deployed, the backstop delivery device 310 may be removed from the endoscope 305, e.g., retracted in a proximal direction and withdrawn from the patient.

Referring now to FIG. 3D at step 300d, a tissue resecting device 360 may be inserted at the proximal end 305a and extended through a working channel of the endoscope 305 to the distal end 305b. A tissue resecting device 360 may be any device configured for resecting tissue, such as a cautery tool. The tissue resecting device 360 may be a device separate from the backstop delivery device 310, although it is also envisioned in other embodiments that the tissue resecting device 360 may be integral to the backstop delivery device 310. Similar to the tissue penetrating device as described above, the tip of the tissue resecting device 360 may be bendable in an arc-like curve. For example, a tip of the device may be bendable up to approximately 90° from the axis 302a, e.g., perpendicular to the inner surface 320a. In some embodiments, the device may include steering wires for actuation of the tip at the distal end of the device by a user at the proximal end by a handle. In some embodiments, the endoscope may be actuatable so that a user may direct the device to be approximately parallel to the tissue wall. The tissue resecting device 360 may have a distal end 360b and a proximal end 360a, and the proximal end 360a may be connected to a power source for generating energy to the distal end 360b for cauterizing. The distal end 360b of the tissue resecting device 360 may be positioned at the tissue selected for resection 315. For example, a distal cautery tip 365 may be positionable in a direction along the axis 302b, for penetrating from an inner surface 320a of the body lumen 320 through the outer surface 320b of the body lumen 320. The tip 365 may cut, burn, sear, or otherwise penetrate through tissue to resect the tissue selected for resection 315.

The tissue resecting device 360 may cauterize around a perimeter 367 of the edge 345 of the covering 340. For example, the perimeter 367 may be internal to the edge 345, so that the anchoring mechanism 350 embedded in body lumen tissue 320 may not migrate and/or release from surrounding tissue during a tissue resection procedure. The tip 365 may penetrate into the tissue (e.g., cut and cauterize)

around the perimeter 367 to separate the tissue selected for resection 315 from the body lumen 320 but without damaging the covering 340. The tip 365 may penetrate entirely through the tissue, e.g., from the inner surface 320a through the outer surface 320b of the body lumen 320. In embodiments, a medical professional may visualize the perimeter 367 for resecting internal to the edge 345 of the covering 340 by fluoroscopy. In some embodiments, an identification gel (e.g., blue identification gel such as a fibrin glue and/or a bioabsorbable scaffold) may be injected between the covering 340 and the outer surface 320b of the lumen 320 to aid in visualization and to provide an additional barrier between the body lumen 320 and the backstop 335, to minimize and/or eliminate the risk of inadvertently damaging the covering 340. For example, a bioabsorbable material may provide an additional barrier while promoting tissue regrowth to allow for the gap to reseal naturally.

When the tissue selected for resection 315 has been entirely resected around the perimeter 367, the tissue 315 may be extracted from the body lumen 320 and retracted within a working channel of the endoscope 305 in a direction along the axis 302a. In some embodiments, a grasping tool or other device may extend out the distal end 305b of the endoscope 305, for grasping the tissue 315 and drawing the tissue 315 within the endoscope 305. Referring now to FIG. 3E, at step 300e, when the tissue 315 has been resected, the body lumen 320 may have a gap 370, e.g., a partial circumferential gap around the body lumen 320. The covering 340 of the backstop 335 may extend entirely over the gap 370 in the body lumen 320, which may be a sterile barrier to minimize and/or avoid a risk sepsis or other contamination of body fluids surrounding the body lumen 320. As described above, the anchoring mechanism 350 may be embedded in tissue of the body lumen 320 around the gap 370 sufficiently external to the perimeter 367 for tissue resection. This may ensure the anchoring mechanism 350 is not dislodged from body lumen 320 so the covering 340 may remain secure over the gap 370 when the tissue 315 has been resected. In some embodiments, the anchoring mechanism 350 may be 10 mm or greater from the perimeter 367 of the gap 370.

The gap 370 may then be closed, so the body lumen 320 is continuous. This may be done by various methods, including joining the remaining tissue together by mechanical fasteners, adhesive, sutures, or combinations thereof. As shown in FIG. 3F, at step 300f, a material 375 may be deposited to fill the gap 370 in the tissue of the body lumen 320. The material 375 may adhere to the surrounding body lumen tissue, to provide a barrier to prevent leakage of body fluid and other contaminant to/from the body lumen 320.

In some embodiments, the material 375 may be a fibrin, mesh, and/or glue material to join to the body lumen 320. The material 375 may be a flexible material, so that the body lumen 320 may be free to move (e.g., the intestine and/or colon may have natural body movement). The material 375 may encourage tissue regrowth. For example, a fibrin glue or other mesh may adhere to tissue fibers, and may be bioabsorbable and/or biodegradable. In some embodiments, a mesh may have hooks, barbs, or other mechanisms to intertwine and engage with tissue fibers to attach to the body lumen 320. In some embodiments, the backstop 335 may be left in the body. In other embodiments, the backstop 335 may be removable from a patient, e.g., after a period of time sufficient for the material 375 to set to the tissue of the body lumen 320 to mitigate potential leakage.

Figure 3G:
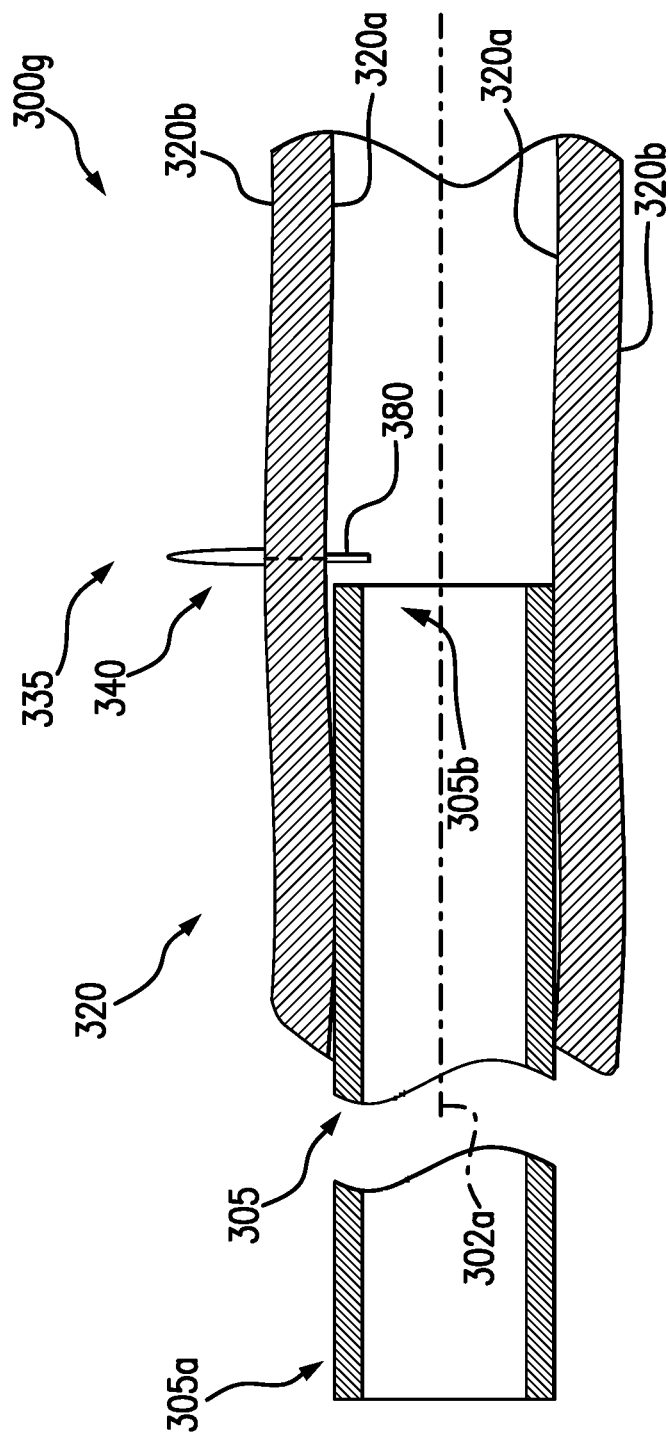

In some embodiments, as shown in FIG. 3G, at step 300g, in addition to and/or as an alternative to step 300f, one or more mechanical fasteners 380 may be used to join the tissue of the body lumen 320 together, e.g., to close the gap 370. For example, one or more Boston Scientific Resolution™ clips, or any other clips, clamps, hemostasis closures, and/or fasteners, may be used to join the tissue of the body lumen 320 to close the gap 370. The mechanical fastener 380 may be delivered to the inner surface 320a of the body lumen 320. The mechanical fastener 380 may be deliverable to the body lumen 320 by the distal end 305b of the endoscope 305, e.g., by a known clip delivery device. A medical professional may visualize placement of the mechanical fastener 380 by a camera or other imaging device of the endoscope 305, and/or an additional visualization device delivered through a working channel of the endoscope 305 and extended beyond the distal end 305b of the endoscope 305 to the body lumen 320. External imaging devices may be used as well to position and confirm placement of the fasteners.

In embodiments, the backstop 335 may be left in the body, and the backstop 335 may be configured to contract and/or expand as the tissue of the body lumen 320 is joined together. For example, the covering 340 may form a greater curvature away from the outer surface 320b of the body lumen 320. As described above, the shape memory material of the covering 340 may result in the covering 340 expanding into a more spherical arc shape. In some embodiments, forces from the shape memory material may be greater than the tissue of the body lumen 320 holding the covering 340, so that the edges 345 of the covering 340 may close together to form a spherical shape, thereby pulling the tissue of the body lumen 320 together and closing the gap 370. At least a portion of the backstop 335 may be formed of a material to encourage tissue regrowth, so that over time, tissue may be fully attached to the backstop 335. For example, the covering 340 may at least partially be formed of an extracellular matrix (ECM) material to encourage cell growth. In some embodiments, the backstop 335 may be removable from a patient, e.g., after a period of time for the material 375 to set to the tissue of the body lumen 320 to mitigate potential leakage. For example, as described above, by using a dual-channel endoscope, a backstop may be operable via one of the working channels while additional tools (e.g., tissue resecting device) may be operable via the other of the working channels. This may allow for the backstop to be easily retractable and/or removable after the procedure is complete.

In some embodiments, additionally and/or alternatively to steps 300f and 300g as shown in FIGS. 3F-3G, a stent 405 may be delivered to the body lumen 320 to close the gap 370. As shown in FIGS. 4A-4C, a stent 405 may be bioabsorbable and may include an extracellular matrix (ECM) material 410 for closing the gap 370 in the body lumen 320. A stent 405 may be used in fully circumferential tissue resection and/or partial tissue resection procedures. The stent 405 may be delivered to the body lumen 320 by a working channel of the endoscope 305, e.g., by known stent delivery devices and techniques.

The stent 405 may be formed as a hollow tube of a self-expanding material, such as a shape memory braided material (e.g., nitinol), and/or bioabsorable material. The stent 405 may have a first end 405a and a second end 405b, and in some embodiments, the first and second ends 405a, 405b of the stent 405 may be uncovered and/or uncoated. This may allow tissue ingrowth to the stent 405, e.g., tissue may grow into the cells or interstices 415 of the braided material of the stent 405, to minimize migration in the body lumen 320. In some embodiments, the stent 405 may include one or more hooks or barbs 420, extending radially from the stent, to engage the inner surface 320*a* of the body lumen 320. The barbs 420 may embed in the body lumen 320 to further minimize and/or prevent migration.

The ECM 410 may be disposed in a central portion 405*c* of the stent 405, so that when the stent 405 is positioned in the body lumen 320, the central portion 405*c* including the ECM 410 may be substantially aligned with the gap 370 of the body lumen 320. The ECM 410 may extend across the stent 405 so that the ECM 410 contacts the entire gap 370, e.g., the perimeter 367 of the gap 370. In some embodiments, at least a portion of the ECM 410 may overlap to at least a portion of the tissue surrounding the gap 370. This overlap may be advantageous for accounting for any axial movement that may occur after placement in the patient, e.g., potential movement of the stent 405 and/or ECM 410 in response to food and/or waste moving through the patient's digestive system. It is understood that the ECM 410 may be formed around a surface 425 of the stent 405, so that body fluid may still flow through the body lumen 320 after the stent 405 is placed. In some embodiments, the ECM 410 may act as a barrier to prevent leakage to/from the body lumen 320. The ECM 410 may be formed of a material to encourage and/or promote tissue cell growth, and may be any of the materials and/or combination of the materials included in the chart illustrated in FIG. 5. As shown in FIG. 4B, new tissue cells 430 may form in the gap 370, so that over time, the body lumen 320 may fully grow to close the gap 370, e.g., so the body lumen 320 is fully closed, as shown in FIG. 4C.

When the gap 370 is closed in the body lumen 320, the stent 405 and/or the ECM 410 may be bioabsorbable and/or biodegradable in the body of the patient, so that after a period of time no additional devices remain in the body lumen 320 of the patient, as illustrated in FIG. 4D. In some embodiments, the stent 405 and/or the ECM 410 may be removable from the patient, using known removal devices and techniques.

Referring now to FIGS. 6A-6C, another embodiment of a resection device, e.g., a stent 600, to secure a body lumen tissue for a resection procedure is shown. The stent 600 may include an elongated hollow body 605 extending along axis 602 and may have a first end 605*a* and a second end 605*b*. The body 605 may be formed of a self-expanding material such as nitinol. In embodiments, the body 605 may be formed of a solid material, e.g., to act as a barrier from contamination of body fluids from outside of the body lumen and as a barrier from contamination with body fluids from inside the body lumen of the area surrounding the body lumen.

The first and second ends 605*a*, 605*b* may have a respective first and second engagement mechanism 610*a*, 610*b*. In some embodiments, the first and second engagement mechanism 610*a*, 610*b* may be a first and second groove 615*a*, 615*b* for receiving a corresponding annular component 622 (e.g., ring or band) and/or other component configured to extend circumferentially around the groove (e.g., suture, adhesive). It is also understood that the first and second engagement mechanism 610*a*, 610*b* may be any mechanism for the stent 600 to engage with the tissue of an inner surface of a body lumen.

The first and second groove 615*a*, 615*b* may extend around the body 605, e.g., about the axis 602. The first and second groove 615*a*, 615*b* may have a curvature, e.g., semi-circular (see FIG. 6B), although other shapes are also envisioned. The first and second groove 615*a*, 615*b* may be any configuration so that a corresponding annular component may mate with the respective groove 615, 615*b*. The first and second groove 615*a*, 615*b* may define three portions of the stent 600, a first flange 620*a* at the first end 605*a*, a second flange 620*b* at the second end 605*b*, and a central portion 620*c* therebetween.

The stent 600 may be deliverable to a body lumen at a location of selected tissue for resection 625 in a direction along the axis 602. The stent 600 may be deliverable by known stent delivery devices, delivering the stent 600 to the location in a constrained state, and then released to an expanded state. The stent 600 may be positionable in the body lumen so that the central portion 620*c* is aligned with the selected tissue for resection 625. When the stent 600 is an expanded state, the first flange 620*a*, the second flange 620*b*, and/or the central portion 620*c* may expand to engage with the inner surface of the body lumen. In some embodiments, the central portion 620*c* may expand only to a point (e.g., less than the circumference of the body lumen), so as to not contact the inner surface of the body lumen. This may be advantageous to avoid inadvertently cutting into the stent 600 during resection. For example, the first and second flanges 620*a*, 620*b* may contact body lumen tissue for engagement, e.g., coupling, with annular components 622. When the first and second flanges 620*a*, 620*b* are coupled with the annular components 622, the central portion 620*c* may be sealed such that it does not contact the tissue wall.

As described above, the central portion 620*c* may be aligned with the selected tissue for resection 625. When the stent 600 is aligned as desired, annular components 622 may be positioned at the first and second engagement mechanism 610*a*, 610*b*. In some embodiments, the annular components 622 may be a multi-piece ring coupleable via fasteners such as magnets or other mechanical joining mechanisms such as clips. In other embodiments, the annular components 622 may be any of a suture, zip tie, or other component, or combinations thereof, for securing the first and second flange 620*a*, 620*b* to the body lumen. The annular components 622 may be configured to mate with the respective first and second engagement mechanism 610*a*, 610*b*, capturing tissue therebetween. For example, the annular component 622 may have an elasticity so that when positioned, the annular component 622 may conform to the circumference of the respective groove 615*a*, 615*b*, with the body lumen tissue proximate to the selected tissue for resection 625 being captured between the stent 600 and the annular component 622. The annular components 622 may seal the body lumen proximate to the selected tissue for resection 625.

When the stent 600 is engaged with the inner surface of the body lumen, the selected tissue may be resected. The stent 600 may be used for partial circumferential resection and/or full circumferential resection. In some embodiments, the selected tissue may be resected from a position outside of the outer surface and inward starting from the outer surface. For example, tissue resecting devices and other accessories may be delivered from outside of the body lumen. In other embodiments, the selected tissue may be resected from within the body lumen and outward starting from the inner surface. For example, the body 605 may include a window 630. A window 630 may be advantageous for delivering accessories (e.g., tissue capture device, tissue resecting device, visualization devices, and the like) through the body lumen and resecting the selected tissue for resection 625. The window 630 may be disposed in the central portion 620*c* of the body 605, and may extend partially circumferential around the body 605. It is also envisioned that the window 630 may be disposed on the body in any location that may allow the medical professional to access the body lumen tissue. In some embodiments, after the body lumen tissue has been accessed for the medical procedure, any remaining openings may be closed by mechanical fasteners such as clips, staples, and/or suturing, and the stent 600 may be removed from the patient. The stent 600 may be removable by disengaging the annular components 622 (e.g., cutting the ring, suture, and/or zip tie) from the stent 600.

When the selected tissue has been resected (see FIG. 6C), the stent 600 and the annular components 622 may remain in the patient. As described above, the annular components 622 coupled in the respective groove 615a, 615b may form a seal between the body lumen and the stent 600 to create a barrier. The tissue may be further closed together across the gap between the grooves as described above with respect to FIGS. 3F-3G and/or 4A-4D.

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but still co-operate or interact with each other.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the subject matter of the claims.

What is claimed is:

1. A system for tissue resection in a body lumen of a patient, the system comprising:
    an endoscope;
    a backstop delivery device extendable through the endoscope and positionable in the body lumen at a location of selected tissue for resection;
    a backstop including a covering deployable by the backstop delivery device; and
    a tissue resecting device extendable through the endoscope for resecting the selected tissue for resection;
    wherein the covering:
    is deployable to an outer surface of the body lumen;
    has one or more anchoring mechanisms disposed on an edge thereof and securable to the outer surface of the body lumen;
    is-expandable to cover the selected tissue for resection; and
    is configured, when expanded and secured to the body lumen, to define a space between the covering and the outer surface of the body lumen to provide clearance between the covering and the outer surface of the body lumen during tissue resection.

2. The system according to claim 1, wherein the backstop delivery device includes a tissue penetrating device for insertion into the selected tissue for resection.

3. The system according to claim 2, wherein the tissue penetrating device is extendable partially in the selected tissue for resection so as to stabilize the backstop delivery device.

4. The system according to claim 1, wherein the covering is formed of a self-expanding material, the covering having a relaxed shape memory curvature, when expanded, forming an arc shape maintaining a working space between the covering and the selected tissue for resection.

5. The system according to claim 4, wherein the arc shape of the curvature and the edge of the covering is conformable to a curvature of the outer surface of the body lumen.

6. The system according to claim 1, wherein the one or more anchoring mechanisms is a mechanical fastener, a suture, or an adhesive, or combinations thereof.

7. The system according to claim 6, wherein the mechanical fasteners are hooks, barbs, clips, or clamps, or combinations thereof.

8. The system according to claim 7, wherein the tissue resecting device is a cautery tool including a distal tip for cauterizing tissue around a perimeter of the selected tissue for resection.

9. The system according to claim 1, wherein the edge of the covering of the backstop is configured:
    to ensure a sterile barrier from the outer surface of the body lumen when secured to the body lumen; and
    to extend beyond the perimeter of the selected tissue for resection such that the one or more anchoring mechanisms remain secured to the outer surface of the body lumen after resection of the selected tissue.

* * * * *